United States Patent [19]

Buckland

[11] Patent Number: 5,332,826
[45] Date of Patent: Jul. 26, 1994

[54] PROCESS FOR PREPARING AMINOACETONITRILES IN ONE VESSEL

[75] Inventor: Paul R. Buckland, Rochester, N.Y.

[73] Assignee: Eastman Kodak Company, Rochester, N.Y.

[21] Appl. No.: 136,432

[22] Filed: Oct. 13, 1993

[51] Int. Cl.$^5$ ............... C07C 253/16; C07C 253/30; C07D 213/57

[52] U.S. Cl. ...................... 546/330; 549/74; 549/75; 549/491; 558/351; 558/408; 558/430; 558/432; 558/433; 558/434; 558/452

[58] Field of Search ............ 558/351, 408, 452; 549/75, 491; 546/330

[56] References Cited

U.S. PATENT DOCUMENTS

| Re. 32,952 | 6/1989 | Krepski et al. | 558/351 X |
| 4,859,784 | 8/1989 | Effenberger et al. | 558/351 X |
| 5,169,973 | 12/1992 | Gibson et al. | 558/351 |

OTHER PUBLICATIONS

"Facile Synthesis of α-Aminonitriles", Khuong Mai et al, *Tetrahedron Letters* vol. 25, No. 41, pp. 4583–4586, (1984).
"A Fast N-Substituted α-Aminonitrile Synthesis", Khuong Mai et al, *Synthetic Communications* 15 (2), 157–163 (1985).

*Primary Examiner*—Joseph Paul Brust
*Attorney, Agent, or Firm*—John D. Thallemer

[57] ABSTRACT

This invention relates to a process for preparing aminoacetonitriles in one vessel. The process involves the steps of: (A) reacting an alkali metal cyanide with an aldehyde in water to form a cyanohydrin; (B) extracting the cyanohydrin formed in Step (A) into a water immiscible solvent to form a two phase system comprising a water immiscible phase containing the cyanohydrin and an aqueous phase; (C) removing at least 50 weight percent, based on the weight of the water immiscible phase, of the water immiscible solvent from the water immiscible phase thereby concentrating the cyanohydrin; (D) adding a water miscible amide solvent to the concentrated cyanohydrin to form a cyanohydrin solution; and (E) passing ammonia through the cyanohydrin solution to obtain an aminoacetonitrile. Aminoacetonitriles are important intermediates in the preparation of amino acids, thiadiazoles, acylaminoacetonitriles, and imidazole derivatives.

3 Claims, No Drawings

PROCESS FOR PREPARING AMINOACETONITRILES IN ONE VESSEL

FIELD OF THE INVENTION

This invention relates to a process for preparing aminoacetonitriles in one vessel. The process involves the steps of: (A) reacting an alkali metal cyanide with an aldehyde in water to form a cyanohydrin; (B) extracting the cyanohydrin formed in Step (A) into a water immiscible solvent to form a two phase system comprising a water immiscible phase containing the cyanohydrin and an aqueous phase; (C) removing at least 50 weight percent, based on the weight of the water immiscible phase, of the water immiscible solvent from the water immiscible phase thereby concentrating the cyanohydrin; (D) adding a water miscible amide solvent to the concentrated Cyanohydrin to form a cyanohydrin solution; and (E) passing ammonia through the cyanohydrin solution to obtain an aminoacetonitrile. Aminoacetonitriles are important intermediates in the preparation of amino acids, thiadiazoles, acylaminoacetonitriles, and imidazole derivatives.

BACKGROUND OF THE INVENTION

Aminoacetonitriles have been prepared by reacting aldehydes with alkali metal cyanides followed by isolation of the cyanohydrin and subsequent reaction with ammonia in a suitable solvent. Isolation of the cyanohydrin can be difficult due to the solubility of cyanohydrin in aqueous medium. Moreover, isolation of the cyanohydrin is inconvenient and increases the risk of exposure to hydrogen cyanide.

Aminoacetonitriles have also been prepared without isolation of the cyanohydrin by the Strecker synthesis using an alkali metal cyanide and an ammonium salt under aqueous conditions. The Strecker synthesis, however, is not practical in cases where the aminoacetonitriles are subsequently used under nonaqueous conditions because it is difficult to isolate the aminoacetonitriles which are unstable and often water soluble.

In contrast, the present inventor has determined that cyanohydrins can be efficiently extracted into volatile water immiscible solvents such as ethyl acetate, thus, avoiding the problem of isolating the aminoacetonitriles. The solvent is removed to give the cyanohydrin, preferably as an oil, which is dissolved in a water miscible amide solvent and reacted with ammonia in the same vessel. Amide solvents are relatively involatile, thus, allowing passage of ammonia to occur over several hours without incurring significant solvent loss. Furthermore, clean conversion to the aminoacetonitriles occurs when amide solvents are used. The use of amide solvents allows the aminoacetonitriles to be converted to important intermediates such as thiadiazoles and acylamino derivatives. Other solvents are not as useful in these respects. For example, use of pyridine or acetonitrile as solvents in the amination step leads to the formation of by-products.

The process of the present invention for preparing aminoacetonitriles and thereafter thiadiazole derivatives is represented as follows.

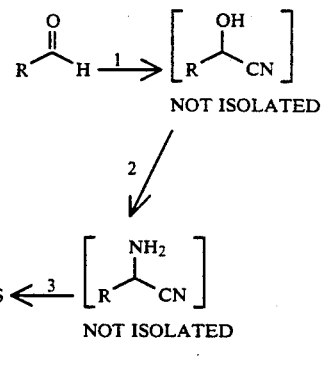

Reagents/solvents: (1) alkali metal cyanide, mineral acid, water, extract with water immiscible solvent; (2) amide solvent, ammonia; and (3) sulfur monochloride.

SUMMARY OF THE INVENTION

Accordingly, it is one object of the present invention to provide a process for preparing aminoacetonitriles.

Accordingly, it is another object of the invention to provide a process for preparing aminoacetonitriles in one vessel.

These and other objects are accomplished herein by a process for preparing aminoacetonitriles in one vessel, said process comprising:

(A) reacting an alkali metal cyanide with an aldehyde at a temperature of $-10°$ C. to $25°$ C. in water to form a cyanohydrin;

(B) extracting the cyanohydin formed in Step (A) into a water immiscible solvent having a boiling point of less than $100°$ C. to form a two phase system comprising a water immiscible phase containing the cyanohydrin and an aqueous phase;

(C) removing at least 50 weight percent, based on the weight of the water immiscible phase, of the water immiscible solvent from the water immiscible phase thereby concentrating the cyanohydrin;

(D) adding a water miscible amide solvent to the concentrated cyanohydrin to form a cyanohydrin solution; and (E) passing ammonia through the cyanohydrin solution to obtain an aminoacetonitrile.

DESCRIPTION OF THE INVENTION

The process of the present invention for preparing aminoacetonitriles in one vessel involves five steps. In the first step, Step (A), an alkali metal cyanide and an aldehyde are reacted at a temperature of $-10°$ C. to $25°$ C. in water to form a cyanohydrin. Preferably the alkali metal cyanide and aldehyde are reacted at a temperature of $-5°$ C. to $5°$ C. The alkali metal cyanide is preferably potassium cyanide or sodium cyanide. The aldehyde has the general formula RCHO and is characterized by an unsaturated carbonyl group (C=O). The R group is selected from hydrogen, unsubstituted or substituted straight chain or branched $C_1$-$C_{20}$ alkyl, unsubstituted or substituted $C_3$-$C_8$ cycloalkyl, $C_3$-$C_8$ alkenyl, $C_3$-$C_8$ alkynyl, and $C_6$-$C_{14}$ aryl.

The unsubstituted and substituted $C_3$-$C_8$ cycloalkyl groups mentioned above refer to cycloaliphatic hydrocarbon groups which contain 3 to 8 carbons in the ring, preferably 5 or 6 carbons, and these cycloalkyl groups substituted with one or two of $C_1$-$C_4$ alkyl, $C_1$-$C_4$ alkoxy, hydroxy or $C_1$-$C_4$ alkanoyloxy.

The $C_3$-$C_8$ alkenyl and $C_3$-$C_8$ alkynyl groups represent straight or branched chain hydrocarbon radicals containing 3 to 8 carbons in the chain and which contain a carbon-carbon double bond or a carbon-carbon triple bond, respectively.

The term "aryl" is used to include carbocyclic aryl groups containing up to fourteen carbons, e.g., phenyl and naphthyl, and those substituted with one or two groups selected from $C_1$-$C_4$-alkyl, $C_1$-$C_4$ alkoxy, $C_1$-$C_4$-alkoxycarbonyl, $C_1$-$C_4$-alkanoyloxy, $C_1$-$C_4$-alkanoylamino, halogen, cyano, $C_1$-$C_4$-alkylsulfonyl, $C_1$-$C_4$-alkylene-$(OH)_n$, $O$—$C_1$-$C_4$-alkylene-$(OH)_n$, —S—$C_1$-$C_4$-alkylene-$(OH)_n$, -$SO_2$-$C_1$-$C_4$-alkylene-$(OH)_n$, -$CO_2$-$C_1$-$C_4$-alkylene-$(OH)_n$, $SO_2N(R_{17})C_1$-$C_4$-alkylene-$(OH)_n$, —$SO_2N(C_1$—$C_4$-alkylene-$OH)_2$, —CON $(R_{17})C_1$-$C_4$-alkylene-$(OH)_n$, —CON $(C_1$-$C_4$-alkylene-$OH)_2$, —N $(SO_2C_1$-$C_4$-alkyl)-alkylene-$(OH)_n$ or —$N(SO_2$ phenyl)-$C_1$-$C_4$-alkylene-$(OH)_n$; wherein n is one or two.

The term "aryl" is also used to include heterocyclic aryl groups such as a 5 or 6-membered heterocyclic aromatic ring containing one oxygen atom, and/or one sulfur atom, and/or up to three nitrogen atoms, said heterocyclic aryl ring optionally fused to one or two phenyl rings or another 5 or 6-membered heteroaryl ring. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazoly, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl, and the like and those rings substituted with one or more substituents listed above in the definition of the term "aryl".

In addition, the term "aryl" includes arylene groups. The term "arylene" is used to represent a divalent carbocylic aryl hydrocarbon moiety containing up to fourteen carbons, e.g., o-, m- and p-phenylene, and those substituted with one or two groups selected from $C_1$-$C_4$-alkyl, $C_1$-$C_4$-alkoxy or halogen. Examples of suitable aldehydes for use in the process of this invention are: p-anisaldehyde, thiophene-2-carboxaldehyde, furan-2-carboxaldehyde, benzaldehyde, crotonaldehyde, trimethylacetaldehyde, acetaldehyde, 4-methylbenzaldehyde, 4-N,N-dimethylaminobenzaldehyde, 3-pyridinecarboxaldehyde, valeraldehyde, and 2-chlorobenzaldehyde. It is important to note that the use of 3-nitrobenzaldehyde as the aldehyde in the process of the present invention does not result in the desired aminoacetonitrile.

In the second step, Step (B), the cyanohydrin formed in Step (A) is extracted into a water immiscible solvent to form a two phase system comprising a water immiscible phase containing the cyanohydrin and an aqueous phase. The aqueous phase is discarded. The water immiscible extraction solvent preferably has a boiling point of less than 100° C. Suitable water immiscible extraction solvents include dichloromethane, ethyl acetate, diethyl ether, chloroform, 1,2-dichloroetbane, methyl acetate, propyl acetate, methyl propionate, methyl butyrate, dimethyl malonate, isobutyl acetate, methylisobutyl ketone, and mixtures thereof. Dichloromethane and ethyl acetate are the preferred water immiscible solvents. It is not unusual to repeat the extraction. It should be noted that toluene and heptanes are not efficient solvents for the extraction of the cyanohydrin.

In the third step, Step (C), at least 50 weight percent of the water immiscible solvent, based on the weight of the water immiscible phase, is removed by distillation at atmospheric or reduced pressure from the water immiscible phase thereby concentrating the cyanohydrin. Preferably, at least 90 weight percent of the water immiscible solvent is removed from the water immiscible phase. Most preferably, the cyanohydrin is concentrated to the degree that it is essentially free from water immiscible solvent. For the most part, any water immiscible solvent remaining with the cyanohydrin will be volatilized upon passage of ammonia in Step (E) supra.

In the fourth step, Step (D), a water miscible amide solvent is added to the concentrated cyanohydrin from Step (C) to form a cyanohydrin solution. Suitable water miscible amide solvents for use in the processes of the present invention are: N,N-dimethylformamide, N,N-diethylformamide, N,N-dimethylacetamide, N,N-diethylacetamide, N,N-dimethylpropionamide, N,N-diethylpropionamide and formamide. The water miscible amide solvent may also include a combination of such solvents. The use of pyridine or acetonitrile as solvents in the amination step leads to the formation of by-products.

In the fifth step, Step (E), ammonia is passed through the cyanohydrin solution from Step (D) to obtain an aminoacetonitrile. Steps (B), (C), (D), and (E) are conducted at a temperature from 20° C. to 50° C. A preferred temperature range is 30C. to 40C. Although higher temperatures may be employed, there is no advantage to conducting these reactions at higher temperatures. Moreover, at temperatures above 50C., the aminolysis reaction requires the use of pressurized equipment.

The aminoacetonitriles are important intermediates in the preparation of amino acids, thiadiazoles, acylaminoacetonitriles, and imidazole derivatives. It is important to note, however, that aminoacetonitriles containing primary and secondary alkyl groups are not useful when the desired product is a thiadiazole. For example, where the aminoacetonitrile contains an n-butyl group, reaction with sulfur monochloride results in a complex mixture which does not contain any thiadiazole. Sulfur monochloride may be reacted with the aminoacetonitriles to obtain 3-chloro-4-substituted-1,2,5-thiadiazoles which are useful as intermediates in the synthesis of M1 selective muscarinic agonists, analgesics, antiglaucoma drugs and for treating Alzheimer's disease. Alternatively, the aminoacetonitriles may be reacted with heterocyclic acid chlorides to obtain carboxamide derivatives which are useful as intermediates for agrochemical fungicides and microbicides.

Examples of agrochemical carboxamide intermediates derived from aminoacetonitriles include:

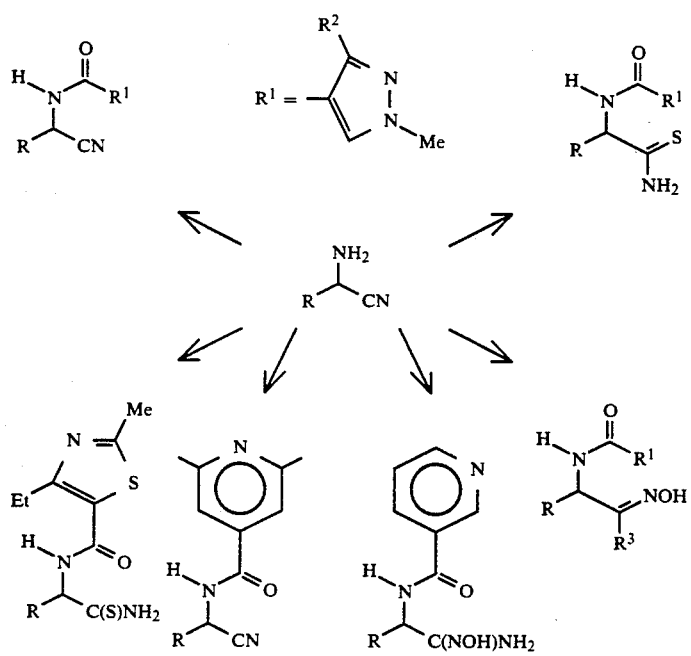

The process of the present invention will be further illustrated by a consideration of the following examples, which are intended to be exemplary of the invention. All parts and percentages in the examples are on a weight basis unless otherwise stated.

EXAMPLE I

Preparation of 3-(4-CHLORO-1,2,5-THIADIAZOL-3-YL) PYRIDINE

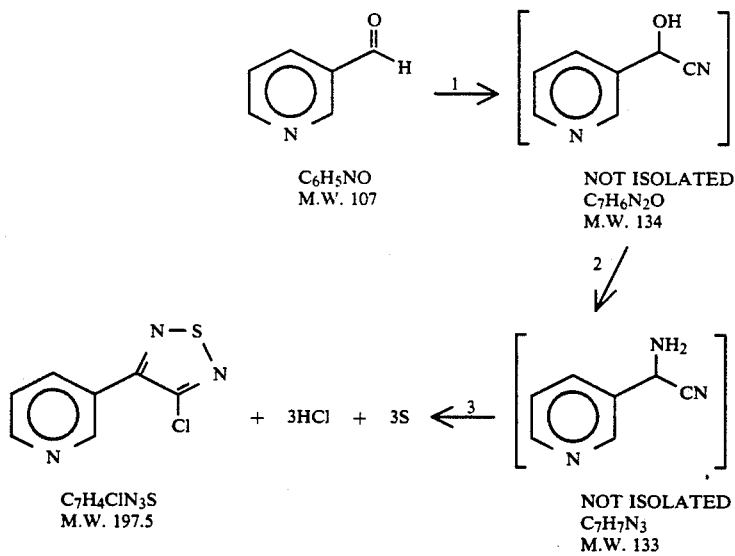

Reagents/Solvents
1. Potassium cyanide, water, 11.6M-hydrochloric acid, ethyl acetate;
2. N,N-dimethylformamide (DMF), ammonia (excess); and
3. Sulfur monochloride.

EXAMPLE II

Preparation of 2-Hydroxy-2(3-pyridinyl)acetonitrile.

11.6M-Hydrochloric acid (18 ml, 21.6 g, 0.2 mole) and 17 ml water were added to a 200 ml three necked flask equipped with an overhead stirrer, thermometer and dropping funnel. The solution was cooled to 0° C. and 97% 3-pyridinecarboxaldehyde (21.4 g, 0.2 mole) was added. The mixture was cooled to −5° C. to give a slurry of pyridinecarboxaldehyde hydrochloride. A solution of potassium cyanide (14.32 g, 0.22 mole) and 40 grams of water was added dropwise to the stirred mixture over 30 minutes, during which the temperature was maintained at −5° C. to −1° C. During the addition a yellow solution was obtained after approximately half the cyanide solution has been added but a slurry is again formed towards the end of the addition. The reaction was mildly exothermic. Stirring was continued for one hour after the addition was complete. 1M-hydrochloric acid (1 ml) was added to bring the mixture to pH 7. Ethyl acetate (70 ml) was added and the mixture warmed to 10° C. whereupon two clear layers were obtained. A 0.5 ml sample of the ethyl acetate layer was removed and evaporated to give a white solid with a melting point of 71° to 73° C. An NMR spectrum was consistent with the desired cyanohydrin.

The bottom aqueous layer was run off and treated with bleach before discarding. Ethyl acetate was removed at reduced pressure (65mm) over 30 minutes using an oil bath set at 70° C. to give a mobile paste. The NMR spectrum (DMF/CDCl$_3$) of the paste was consistent with the desired product (CH at d=5.7) and showed that no aldehyde starting material was present. This implies that the yield of the product is quantitative. The product was dissolved in N,N-dimethylformamide and treated with ammonia.

EXAMPLE III

Preparation of 2-Amino-2-(3-pyridil)acetonitrile

N,N-Dimethylformamide (100 ml) was added to the paste to give a pale yellow solution. Ammonia was passed, via a sintered glass tube, through the solution for 68 hours at 25° C. to give a reddish orange solution of the aminonitrile. The mixture was periodically analyzed by NMR spectroscopy. The temperature rose initially from 24° C. to 34° C. and the mixture became a deeper yellow color.

NMR analysis showed that very little cyanohydrin (CH at 5.7 ppm) remained after 44 hours (product CH at 5.1 ppm). However several other smaller signals close to 5.1 ppm were also observed during this time hut disappeared after 68:hours. One of the smaller signals may he due to the CH of the deprotonated cyanohydrin. Excess ammonia was removed at 65 mm by application of water pump pressure for 1 hour.

EXAMPLE IV

Preparation of 3-(4-chloro-1,2,5-thiadiazol-3-YL)pyridine

Supercell T (10 g) was added to the solution of aminonitrile prepared in Example 3 (assume 0.18 mole) in DMF (approx. 100 ml), in a 200 ml flask. (Supercell T was added to prevent the coagulation of the sulfur formed during the reaction involving sulfur monochloride). The mixture was cooled to −15° C. and sulfur monochloride (49 g, 29 ml, 0.36 mole) was added dropwise with stirring over 40 minutes, so that the temperature was maintained at −10° to −3° C. An acetone/solid carbon dioxide bath was used.

The reaction was very exothermic particularly during addition of the first 25% of the sulfur monochloride which required 1 hour in order to keep the temperature at −5° to 0° C. The mixture was cooled to 0° C. and ice cold water (100 g) was added over 15 minutes. The mixture was stirred for 12 hours. Sulfur and supercell T were removed by filtration into a 500 ml flask and the residue washed with 20 grams of water. The damp residue weighed 42 grams. The combined filtrates were cooled to 0° C. and toluene (100 ml, water (87 g) was added. A mixture of sodium hydroxide (27 g, 0.675 mole) and water (27 g) was added over 15 minutes, keeping the temperature at 10° to 15° C. to bring the mixture to pH 9. Supercell T (10 g) and water (50 g) were added and the mixture was stirred for 15 minutes and then partially filtered back into the original 200 ml flask.

The bottom aqueous layer was run off and discarded. (A flashlight is useful for detecting the interface between the two dark layers). The remaining material in the 500 ml flask was filtered into a 200 ml flask and the layers were separated as before. The total aqueous solution discarded was 300 ml. Extraction of this solution with toluene (50 ml) and evaporation of the toluene gave only a further 1 g product. The residue was washed with toluene (20 ml, 17.3 g). The combined filtrates were washed with 50 grams of water and the lower aqueous layer (53 g) was discarded. The upper toluene layer (120 g, approx. 138 ml) was evaporated at 45° C. at reduced pressure to give 20 grams of crude product which appeared as a brownish orange oil.

Heptanes (150 ml, 102 g) was added to the oil and the mixture stirred and heated to 45° C. After 30 minutes, the clear yellow supernatent was filtered into the 500 ml flask to remove 2 grams of a dark brown insoluble residue. The heptanes solution was transferred back to a clean 200 ml flask and evaporated under reduced pressure at 45° C. to give 17 grams of an orange oil which crystallized on cooling. Thin layer Chromatography showed that most of the impurities which had lower Rfs than the product had been removed. An NMR spectrum was consistent with the desired product + solvents (heptanes, toluene, DMF). HPLC indicated that the product was 98.5% pure.

The product was dissolved in methanol (30 ml) at 30° C. to give a clear solution which was then cooled to 20° C. (The supercell treatments used in this experiment appear to effectively remove the sulfur and make filtration at this stage, unnecessary). Water (60 ml) was added dropwise with stirring until a permanent cloudiness was obtained. The mixture was seeded and stirring continued until crystallization began. Stirrer speed was increased and the remaining water added more rapidly. The solid was collected and washed with 15 grams water which had been used to rinse out the flask.

The solid material, 28 grams, was dried under vacuum for 48 hours at 30° C. to give 99% pure 3-(4-chloro-1,2,5-thiadiazol-3-yl)pyridine (16 g, 45% yield) as a pale yellow solid with a melting point of 51° to 52C. NMR data was as follows: (CDCl$_3$, ppm) 7.46 (dd, 1H), 8,29 (dt, 1H), 8.75 (dd, 1H), 9,24 (d, 1H).

Many variations will suggest themselves to those skilled in this art in light of the above detailed description. All such obvious modifications are within the full intended scope of the appended claims.

What is claimed is:

1. A process for preparing aminoacetonitriles comprising the steps of:
    (A) reacting an alkali metalcyanide with an aldehyde having the formula RCHO at a temperature of −10° C. to 25° C. in water to form a cyanohydrin, wherein R is selected from the group consisting of hydrogen, $C_1$–$C_{20}$ alkyl, $C_3$–$C_8$ cycloalkyl, $C_3$–$C_8$ alkenyl, $C_3$–$C_8$ alkynyl, and $C_6$–$C_{14}$ aryl, excluding 3-nitrobenzaldehyde;
    (B) adding a water immiscible solvent to the cyanohydrin formed in Step (A) to form a two phase system comprising a water immiscible phase containing the cyanohydrin and an aqueous phase;
    (C) removing at least 50 weight percent, based on the weight of the water immiscible phase, of the water immiscible solvent from the water immiscible phase thereby concentrating the cyanohydrin;

(D) adding a water miscible amide solvent to the concentrated cyanohydrin to form a cyanohydrin solution; and (E) passing ammonia through the cyanohydrin solution to obtain an aminoacetonitrile, provided steps (B), (C), (D), and (E) are conducted at a temperature of 20° C. to 50° C, and further provided that steps (A), (B), (C), (D), and (E) are conducted in the same reaction vessel wherein the cyanohydrin is not isolated.

2. A process for preparing aminoacetonitriles comprising the steps of:

(A) reacting an alkali metal cyanide with an aldehyde at a temperature of −10° C. to 25° C. in water to form a cyanohydrin, wherein the alkali metal cyanide is selected from the group consisting of sodium cyanide, potassium cyanide, lithium cyanide and cesium cyanide, and the aldehyde is selected from the group consisting of p-anisaldehyde, thiophene-2-carboxaldehyde, furan-2-carboxaldehyde, benzaldehyde, crotonaldehyde, trimethylacetaldehyde, acetaldehyde, 4-methylbenzaldehyde, 4N,N-dimethylaminobenzaldehyde, 3-pyridinecarboxaldehyde, valeraldehyde, and 2-chlorobenzaldehyde;

(B) adding a water immiscible solvent to the cyanohydrin formed in Step (A) to from a two phase system comprising a water immiscible phase containing the cyanohydrin and an aqueous phase, wherein the water immiscible solvent is selected from the group consisting of dichloromethane, ethyl acetate, diethyl ether, chloroform, 1,2-dichloroethane, methyl acetate, propyl acetate, methyl propionate, methyl butyrate, dimethyl malonate, isobutyl acetate, methylisobutyl ketone, and combinations thereof; removing at least 50 weight percent, based on the weight of the water immiscible phase, of the water immiscible solvent from the water immiscible phase thereby concentrating the cyanohydrin;

(D) adding a water miscible amide solvent to the concentrated cyanohydrin to form a cyanohydrin solution, wherein the water miscible amide solvent is selected from the group consisting of N,N-dimethylformamide, N,N-diethylformamide, N,N-dimethylacetamide, N,N-diethylacetamide, N,N-dimethylpropionamide, N,N-diethylpropionamide, formamide, and combinations thereof; and (E) passing ammonia through the cyanohydrin solution to obtain an aminoacetonitrile, provided steps (B), (C), (D), and (E) are conducted at a temperature of 20° C. to 50° C., and further provided that steps (A), (B), (C), (D), and (E) are conducted in the same reaction vessel wherein the cyanohydrin is not isolated.

3. A process for preparing aminoacetonitriles comprising the steps of:

(A) reacting an alkali metal cyanide with 3-pyridinecarboxaldehyde at a temperature of −5° C. to 5° C. in water to form a cyanohydrin, wherein the alkali metal cyanide is selected from the group consisting of sodium cyanide and potassium cyanide;

(B) adding a water immiscible solvent to the cyanohydrin formed in Step (A) to form a two phase system comprising a water immiscible phase containing the cyanohydrin and an aqueous phase, wherein the water immiscible solvent is selected from the group consisting of dichloromethane and ethyl acetate;

(C) removing at least 50 weight percent, based on the weight of the water immiscible phase, of the water immiscible solvent from the water immiscible phase thereby concentrating the cyanohydrin;

(D) adding N,N-dimethylformamide to the concentrated cyanohydrin to form a cyanohydrin solution; and (E) passing ammonia through the cyanohydrin solution to obtain an aminoacetonitrile, provided steps (B), (C), (D), and (E) are conducted at a temperature of 30° C. to 40° C., and further provided the steps (A), (B), (C), (D), and (E) are conducted in the same reaction vessel wherein the cyanohydrin is not isolated.

* * * * *